(12) United States Patent
Jeong et al.

(10) Patent No.: US 11,547,640 B2
(45) Date of Patent: Jan. 10, 2023

(54) ADHESIVE PATCH TO ORAL CAVITY HAVING IMPROVED STABILITY AND USABILITY

(71) Applicant: LG HOUSEHOLD & HEALTH CARE LTD., Seoul (KR)

(72) Inventors: Yong-Beom Jeong, Seoul (KR); Seong-Eun Bang, Seoul (KR); Jae-Hyun Ahn, Seoul (KR)

(73) Assignee: LG HOUSEHOLD & HEALTH CARE LTD., Seoul (KR)

( * ) Notice: Subject to any disclaimer, the term of this patent is extended or adjusted under 35 U.S.C. 154(b) by 12 days.

(21) Appl. No.: 17/304,901

(22) Filed: Jun. 28, 2021

(65) Prior Publication Data
US 2021/0401676 A1 Dec. 30, 2021

(30) Foreign Application Priority Data

Jun. 29, 2020 (KR) .................. 10-2020-0079626
Apr. 27, 2021 (KR) .................. 10-2021-0054657

(51) Int. Cl.
| | | |
|---|---|---|
| *A61K 8/02* | (2006.01) | |
| *A61K 8/81* | (2006.01) | |
| *A61Q 11/00* | (2006.01) | |
| *A61K 8/73* | (2006.01) | |
| *A61K 8/22* | (2006.01) | |

(52) U.S. Cl.
CPC .............. *A61K 8/0208* (2013.01); *A61K 8/22* (2013.01); *A61K 8/731* (2013.01); *A61K 8/8111* (2013.01); *A61Q 11/00* (2013.01)

(58) Field of Classification Search
CPC .................................. A61K 8/02; A61K 8/03
USPC .......................................... 433/217.1; 424/53
IPC ....................................................... A61Q 11/00
See application file for complete search history.

(56) References Cited

U.S. PATENT DOCUMENTS

2010/0040840 A1* 2/2010 Saito ........................ C08J 7/043
526/321

FOREIGN PATENT DOCUMENTS

| KR | 1020020045224 | * | 6/2002 | ................ A61K 8/22 |
| KR | 1020030044968 | * | 11/2005 | ................ A61K 8/02 |
| KR | 1020030080027 | * | 2/2006 | ................ A61K 8/02 |
| WO | 2014/062879 A2 | | 4/2014 | |

* cited by examiner

*Primary Examiner* — Walter E Webb
(74) *Attorney, Agent, or Firm* — Vorys, Sater, Seymour and Pease LLP; Mih Suhn Koh

(57) ABSTRACT

The present disclosure provides a patch which is attached to a tooth or oral mucous membrane and releases an active ingredient to a portion attached, in which the patch comprises a drug layer having an adhesive surface attached to the tooth or oral mucous membrane and a backing layer laminated on the drug layer, and comprises at least one reticular structure inside the drug layer, and is divided into at least 2 drug layers at the boundary of or by the reticular structure.

20 Claims, 9 Drawing Sheets

ADHESIVE PATCH TO ORAL CAVITY HAVING IMPROVED STABILITY AND USABILITY

TECHNICAL FIELD

The present application claims the priority based on Korean Patent Application No. 10-2020-0079626 filed on Jun. 29, 2020 and Korean Patent Application No. 10-2021-0054657 filed on Apr. 27, 2021, and the entire contents disclosed in the description and drawings of the corresponding application are incorporated in the present application. The present disclosure relates to an adhesive patch for applying to an oral cavity, more specifically to a tooth or oral mucous membrane.

BACKGROUND ART

When delivering an active ingredient for tooth whitening, tooth decay prevention, anti-inflammation, or sensitive teeth prevention to intraoral tissue (teeth, gums, mucosa etc.), there is a problem in that the active ingredient is diluted by saliva or swallowed, so that the effect is inferior and uncomfortable feeling occurs during use. In order to solve this problem, an adhesive patch attached to the oral cavity and exhibiting long-term efficacy has been used.

Conventional patch products contain water-soluble polymers having good adhesion to teeth and/or oral tissue, particularly water-soluble polymers having good compatibility with tooth whitening ingredients (for example, hydrogen peroxide). In addition, there are also the patches exhibiting strong adhesion when the drug layer in the patch is hydrated by moisture such as saliva.

However, there have been attempts to improve a large amount of residue in the oral tissue after use, due to the strong adhesion in the oral cavity.

Some products in the market use acrylate-based polymers together with PVP polymers conventionally used as a tooth-attaching polymer to weaken the adhesiveness of the patch and reduce the residue on the oral tissue as a tooth. But there is the problem that the manufacturing process is somewhat complicated because the pre-mixed process of PVP polymer and the acrylate polymer is needed.

The present inventors have discovered that the amount of peroxide-compatible polymer is above the amount required for attachment to the oral cavity in order to secure the stability of hydrogen peroxide, thus a significant amount of the polymer remains on the tooth surface after use.

On the other hand, most of oral patches have a separate backing layer on the drug layer in order to prohibit rapid dilution by saliva and weakened adhesion to teeth. In general, PE film as the backing layer is used. The PE film layer also does not cause breakage in the manufacture or use because of its higher tensile strength and flexibility. In addition, it can be customizable and attachable to the curve of the tooth. However, when patches using a PE film are exposed to certain conditions (ex: high temperature, long-term aging, etc.), there can occur delamination between the drug layer and PE film backing layer, resulting in adhesion between drug layers and contamination of patches products during bulk packaging.

SUMMARY OF THE INVENTION

Technical Problem

Accordingly, the purpose of the present disclosure is to provide a patch for applying to a tooth or oral mucous membrane (oral mucosa), having excellent feeling and quality in use. Specifically, the purpose of the invention is to provide the patch neatly removable without leaving excessive residue upon removal, while having sufficient adhesiveness to a tooth or oral mucous membrane.

Another purpose of present disclosure is to provide the patch stably attached to a tooth or oral mucous membrane without separation, breakage or delamination between the water-insoluble backing layer and drug layer.

Another purpose of present disclosure is to provide a new type of patch, preferably, patch for tooth whitening without separation, breakage or delamination between the water-insoluble backing layer and drug layer.

In addition, another purpose of the present disclosure is to provide the kit comprising the patch, in particular for tooth whitening, and the method for promoting oral health, in particular for whitening tooth comprising the patch or kit.

Technical Solution

One example of the present disclosure provides a patch comprising a reticular structure, for example, mesh. More specifically, one example of the present disclosure provides a patch for applying to a tooth or oral mucosa, comprising a drug layer having an adhesive surface and a backing layer laminated to the drug layer, wherein the drug layer includes at least one reticular structure which divides the drug layer into multiple sections.

The backing layer may comprise a polymer having good binding ability to the drug layer, for example, ethyl cellulose.

The reticular structure may be polyethylene, and may play a role in preventing delamination, breakage or separation of the backing layer. In addition, the reticular structure may also play a role in reducing residue of the base or adhesive polymer on a target site after use.

At least one reticular structure may be comprised inside the drug layer of the patch, and the drug layer may be divided into at least two drug layers by the reticular structure or at the boundary of the reticular structure. The drug layer may comprise the first drug layer and the second drug layer. The first drug layer is the region between the adhesive surface positioned on one side of the drug layer and the reticular structure, and a second drug layer is the region between the first drug layer and the backing layer. In other words, the drug layer comprises the first drug layer, the reticular structure and the second drug layer.

One example of the present disclosure provides a patch to be attached to a tooth or oral mucous membrane and releases an active ingredient to the target site or the attached region. By adhesiveness of the first drug layer, it may be directly attached to the target site or may be attached with hydration of the first drug layer by saliva. When the first drug layer is attached to the target site and the polymer of the first drug layer is hydrated and swelled by the saliva or moisture, the saliva or moisture may pass through the reticular structure and be delivered to the second drug layer. When the saliva or moisture delivered to the second drug layer hydrates and swells the second drug layer, the active ingredient in the second drug layer may pass through the reticular structure and be delivered to the first drug layer and the target site, for example oral mucous membrane or a tooth. The reticular structure positioned between the first drug layer and the second drug layer may have the through hole for movement of the saliva or moisture and an active ingredient. The active ingredient may be comprised in both the first drug layer and the second drug layer, or may be comprised in the second drug layer only. Surely, if necessary, the active ingredient may be comprised in the first drug layer only.

The patch according to one example of the present disclosure comprises peroxide activator in the first drug layer for promoting degradation of peroxides. In this case, the first drug layer preferably does not comprises an active ingredient for whitening tooth and the second drug layer comprises an active ingredient for whitening tooth without peroxide activator. The peroxide activator may activate the efficacy of peroxide delivered from the second drug layer to the first drug layer.

According to one example of the present disclosure, when the patch is used, the backing layer and reticular structure may be removed from the target site together, thus the second drug layer may be removed together. For easiness of removal, the backing layer and reticular structure may be attached to each other at both ends of the patch. By this, without separation, delamination or breakage between the backing layer and reticular structure, the patch may be removed from the target site at once. In addition, the amount of material constituting the second drug layer at both ends of the patch may be smaller than that of other regions. When removed after use of the patch, the residue remaining in target site, for example a tooth or teeth or oral cavity may be minimized because all or part of the first drug layer is dissolved by saliva or moisture, result in good feeling at the time of removal.

The drug layer may comprise two sections of a first drug layer and a second drug layer, wherein the first drug layer is between the adhesive surface and the reticular structure, and the second drug layer is between the first drug layer and the backing layer, and wherein the first drug layer has a thickness of 5 to 50% of the thickness of the total drug layer. The thickness of the first drug layer may be 5 to 50%, preferably 10 to 40%, of the total thickness of the drug layer based on the longitudinal section of the patch.

The reticular structure may have an embo pattern.

The reticular structure may have an embo pattern formed by filaments connection in which at least two filaments meet or cross, and the through holes which the active ingredient passes through may be formed, so the reticular structure may have a plurality of through holes.

The total area of the through hole of the reticular structure may be 10 to 60% relative to the total area of one side of the reticular structure that is horizontal with the adhesive surface of the drug layer.

In the filament connection, 2 filaments may meet or cross, or 3 or more filaments may meet or cross. So the filament connection is formed by two, three or more filaments.

The filaments forming the reticular structure may be spaced apart from 30 to 500%, preferably 50 to 400%, more preferably 60 to 300%, further more preferably 70 to 250% relative to the thickness of the filament.

Each through hole may have an area of at least 0.01 mm$^2$ to 0.5 mm$^2$.

The number of the through holes may be 100 to 800 per 1 cm$^2$ of unit area of the surface of the reticular structure.

In addition, the reticular structure may be manufactured by injection molding method using thermoplastic resin.

For example, the reticular structure may be mesh.

The reticular structure may comprise a through hole and an embo pattern. The embo pattern has a convex portion and a concave portion, and the convex portion of the embo pattern may be formed in the direction of the adhesive surface. In other words, the concave surface is the position where the length perpendicularly drawn up to the reticular structure from the adhesive surface is long, and the convex surface is the surface where the length perpendicularly drawn up to the reticular structure from the adhesive surface is short. At the position of the convex surface, when the amount of the adhesive or base polymer in the first drug layer is no or small, adhesion strength to the tooth or oral mucous membrane may be further weakened. In other words, because the patch having embo pattern has a strong side and a weak side based on the surface of the adhesive surface, it may be removed more easily after use.

In order to be eroded by saliva or moisture, be attached to a target site or to release an active ingredient, the drug layer may comprise a water-soluble, water-swellable or water-dispersible polymer as the base or adhesive polymer.

The polymer may comprise any one or more selected from the group consisting of polyvinyl pyrrolidone, carbomer, pullulan, carrageenan, sodium alginate, acrylate polymer or copolymer, water-soluble cellulose-based polymer, xanthan gum, polyvinyl alcohol, and combination thereof. Preferably, the polymer may be a glassy polymer. Herein, the glassy polymer means a polymer whose adhesive strength is increased by 50% or more upon hydration compared to the dry state.

The drug layer may further comprise any one or more of plasticizers selected from the group consisting of polypropylene glycol, glycerin, or polyethylene glycol, castor oil, PEG-60 hydrogenated castor oil, PEG-40 hydrogenated castor oil, and combination thereof, in addition to the polymer.

The patch may further comprise a backing layer, and the backing layer may be positioned on the opposite side of the adhesive surface of the drug layer.

The backing layer may comprise or consisting of a water-insoluble polymer having a hydrophilic functional group such as a hydroxyl group or carboxyl group, a thermoplastic or a mixture thereof.

The water-insoluble polymer having a hydrophilic functional group may be one or more polymer selected from the group consisting of ethyl cellulose, cellulose acetate, polymethylmethacrylate copolymer, acetate-polyvinyl pyrrolidone copolymer, and combination thereof.

The thermoplastic may be one or more polymer selected from the group consisting of polyethylene, polyethylene terephthalate, polyvinyl chloride, polyvinylidene chloride, polystyrene, polypropylene, and combination thereof.

The reticular structure may comprise one or more of polymer filaments manufactured by using the polymer selected from the group consisting of polyester, nylon, polypropylene, polyethylene, polybutylene terephthalate, ethylene vinyl acetate, and combination thereof. Preferably, the reticular structure may be formed by polyethylene filament, and the reticular structure may comprise an embo pattern.

Herein, "filament" may mean fiber or fiber-like thin strand, and an example of the filament may be natural fiber or thermoplastic fiber, and it is preferable that the filaments are fused by heat to be entangled.

The active ingredient may be a component for whitening tooth, and the patch may be used for whitening tooth.

One example of the present disclosure provides a kit for whitening tooth or teeth.

The kit for whitening a tooth or teeth may comprise the patch releasing component for whitening a tooth and the instruction manual describing the method for using the patch. The patch may comprise a reticular structure inside of it and the drug layer having an adhesive surface attached to the tooth. The reticular structure is comprised inside of the drug layer, thus a part of the drug layer may be present between the reticular structure and the adhesive surface attached to a tooth or teeth.

In the patch according to the invention, backing layer is laminated on the drug layer on the opposite side of the adhesive surface.

The reticular structure may comprise an embo pattern and through holes.

The reticular structure may have an embo pattern formed by the filament connection in which at least 2 or more filaments meet or cross, and the through hole for passing through an active ingredient may be formed in it.

The component for whitening a tooth or teeth may be one or more of peroxides selected from the group consisting of hydrogen peroxide, carbamide peroxide, calcium peroxide, sodium percarbonate, sodium perborate, tetrasodiumpyrophosphate peroxidate and a mixture thereof.

The instruction manual may include instructions including the method for using the patch, wherein comprising removing the patch after attaching it for 30 minutes to one day, preferably 3 minutes to 12 hours, more preferably 5 minutes to 3 hours, further more preferably 10 minutes to 90 minutes.

In one embodiment, a kit for whitening a tooth or teeth comprising the patch according to the invention, a kit for relieving, preventing or inhibiting a sensitive tooth or teeth comprising the patch comprising a component for relieving, preventing or inhibiting sensitive teeth, or a kit for relieving, preventing or inhibiting halitosis comprising the patch comprising a component for removing, relieving or preventing halitosis is provided.

Other example of the present disclosure provides a method for whitening tooth or teeth.

The method for whitening tooth or teeth comprises the patch or kit as disclosed herein.

One example of the present disclosure provides a method for whitening tooth or teeth comprising preparing the patch as disclosed herein, attaching the patch to the target site such as tooth or teeth, and removing the patch after a certain period of time.

The patch may be removed in 10 minutes to 90 minutes after its attachment to the target site.

The method can make tooth or teeth whitened by the tooth whitening component comprised in the drug layer, wherein it passes through the through hole formed in the reticular structure and reach the tooth surface.

One embodiment of the present disclosure provides a method for preparing the patch comprising a reticular structure.

The method may comprise:

(S1) preparing a drug layer preparation solution comprising a water-soluble, water-swellable or water-dispersible polymer as the base or adhesive polymer and an active ingredient, (S2) drying a certain amount of the drug layer preparation solution to form a first drug layer in form of partially or completely dried film, (S3) laminating or applying a reticular structure and then applying the remained amount of the drug layer preparation solution to the first drug layer and drying to form a second drug layer;
and (S4) locating a backing layer on the second drug layer, and then optionally drying.

If necessary, after the above (S4) steps, additional drying step may be comprised.

The drying may be carried out at a temperature of 40 to 60° C.

The backing layer may be formed by applying a backing layer preparation solution comprising a water-insoluble polymer, or may be formed by locating a water-insoluble film previously manufactured.

The thickness of the first drug layer may be 5 to 50% of the total thickness of the drug layer based on the longitudinal section of the patch.

Advantageous Effects

The present disclosure can provide a patch for applying to a tooth or oral mucosa with excellent usability and quality. The patch of the present disclosure has sufficient adhesiveness to a tooth or oral mucosa, but it may be neatly removed without leaving excessive residue upon removal because of lower hydration of the second drug layers. The patch of the present disclosure does not cause breakage, separation or delamination between the drug layer and backing layer when removed, because of its appropriate tensile strength.

BRIEF DESCRIPTION OF DRAWINGS

The following drawings attached to the present description illustrate preferable examples of the present disclosure, and serve to further understand the technical spirit of the present disclosure together with the aforementioned contents of the invention, so the present disclosure should not be interpreted to be limited to the matters described in such drawings.

DETAILED DESCRIPTION OF THE INVENTION

Hereinafter, it will be described in more detail.

Patch (1)

The term mentioned herein, "patch" is a comprehensive meaning which can include all structures in which an adhesive surface is attached to a target site and releases an active ingredient. It may be used by substituting to other terms such as 'drug delivery system', 'strip', 'film', 'tape' and the like, and the contents described herein do not except the terms mentioned above.

Figure 1:
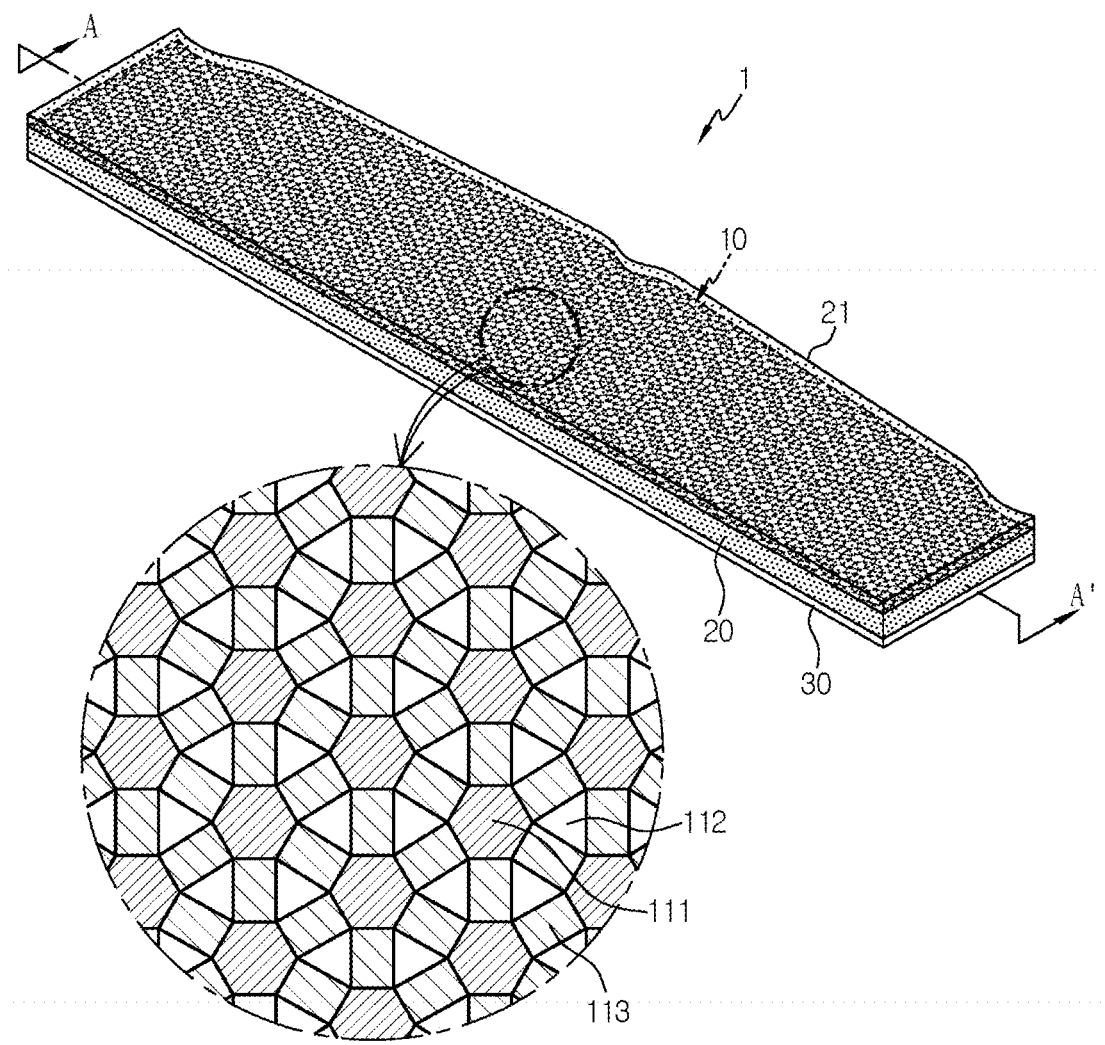
FIG. 1 shows the perspective view to represent one example of the patch according to one embodiment of the present description. In addition, in FIG. 1, a part of the reticular structure (10) present in the drug layer (20) is shown illustratively by being enlarged.

The patch may be attached to a target site such as a tooth or oral mucous membrane, and the "target site" is the site intended for the active ingredient to act, and the tooth or teeth may be understood as an example of the target site for the active ingredient acting on the tooth or teeth, and gum may be understood as an example of the target site for the active ingredient acting on the gum. The term mentioned herein, "oral mucous membrane" may be understood to mean a mucous membrane covering the inner surface of the oral cavity, and may include mucous membrane tissue positioned in 'gum', 'lip', 'tongue' and the like. FIG. 1 shows a perspective view to represent one example of the patch according to one embodiment of the present description. The patch (1) according to one embodiment may comprise a drug layer (20) and a backing layer (30) positioned or laminated on one side of the drug layer. The backing layer (30) may be positioned or laminated on the opposite side of the adhesive surface (21). The drug layer (20) may comprise a reticular structure (10) inside of it, and a part of the drug layer may be present between the reticular structure (10) and the adhesive surface (21). This may be referred to as the first drug layer (20a). Referring to the FIG. 1, saliva or moisture absorbed through the adhesive surface (21) may pass through the through holes (112) in the reticular structure (10) and may be delivered to the region of the drug layer between the backing layer and reticular structure. The region of the drug layer between the backing layer and reticular structure is the second drug layer. The moisture or saliva delivered to the second drug layer may swell the polymer in the second drug layer and may release active ingredients in it. Referring to the enlarged image of the reticular structure of FIG. 1, filaments (113) may be entangled, resulting in embo (111) pattern in some regions of the filaments. The structure of the reticular structure is not limited to the above example, and the reticular structure may be prepared in a woven or non-woven form of thermoplastic radial fiber, or may be provided by injection molding method.

Drug Layer (20)

The patch as disclosed herein comprises the drug layer comprising the reticular structure (10). By comprising at least one reticular structure inside of it, the drug layer may be divided into at least 2 drug layers by the reticular structure or at the boundary of the reticular structure. According to one embodiment, the drug layer (20) may comprise or consist of a first drug layer (20a) and a second drug layer (20b). The first drug layer (20a) has an adhesive surface (21) for contacting to a target site, and is positioned between the adhesive surface (21) and the reticular structure (10). The second drug layer (20b) is positioned between the first drug layer (20a) and the backing layer (30). In the second drug layer (20b), the reticular structure (10) is placed. The composition of the first drug layer (20a) and the second drug layer (20b) may be the same or different. Preferably, they may have the same composition. The first drug layer may be directly attached to the target site, or may be attached with hydration of the first drug layer by saliva or moisture. When the polymer of the first drug layer is hydrated and swelled after the first drug layer is attached to the oral cavity or tooth, the saliva or moisture may be delivered to the second drug layer. The saliva or moisture delivered to the second drug layer may hydrate and swell the second drug layer, resulting in release of the active ingredient in the second drug layer to the first drug layer and thereby delivery to the target site.

The amount of base or adhesive polymer in the first drug layer may be about 5 mg to 50 mg, or about 7 to 40 mg, per unit area 1 $cm^2$ of the adhesive surface.

When adjusting the thickness occupied by the first drug layer in the drug layer, the residue on the tooth surface may be reduced, thereby improving user's feeling at removal after use.

The thickness of the first drug layer present between the reticular structure and the adhesive surface of the patch may be 5 to 50%, preferably 40 to 10% of the total thickness of the drug layer based on the longitudinal section of the patch. Here, the total thickness of the drug layer may comprise the thickness of the reticular structure. For example, the thickness of the first drug layer may be 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, or less.

The thickness (h1) of the first drug layer may be the distance from the adhesive surface (21) to the surface of the reticular structure, in which the first drug layer and the second drug layer meet in the through hole. The distance may be defined as the average length of a line drawn vertically from an arbitrary point of a line formed by connecting two points (P' and P") in contact with the end point of the filament at the through hole portion of the reticular structure to the adhesive surface. In another method, when a vertical line is drawn from the adhesive surface (21) in the direction of the backing layer (30) and the contact point between the vertical line and the reticular structure is P, the h1 may mean a value obtained by dividing the volume of the drug layer between the surface formed by connecting the P and the tooth adhesive surface by the total area of the tooth adhesive surface.

In one embodiment, even when the reticular structure is an embo pattern, the thickness of the first drug layer may be defined in the same manner.

Figure 2:
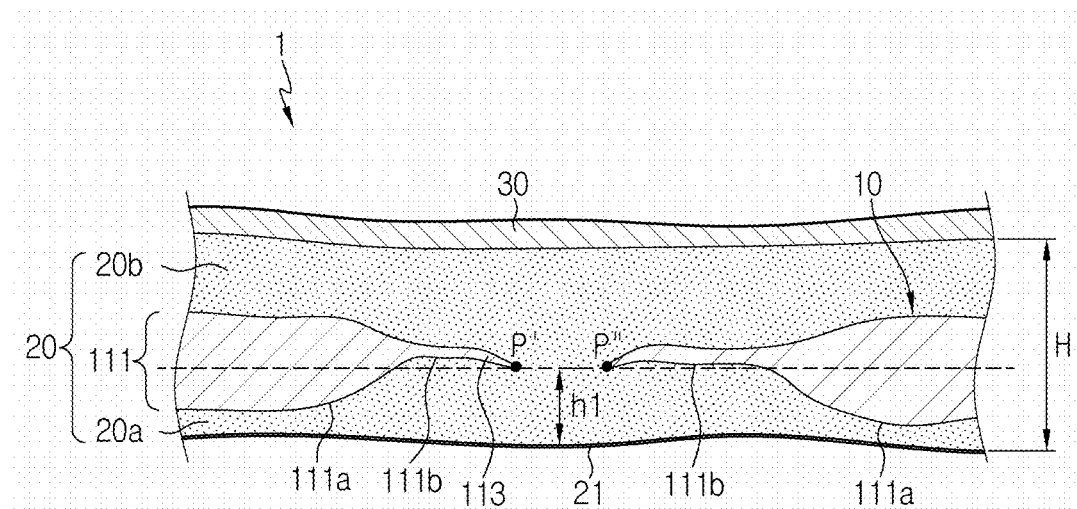
FIG. 2 is a picture illustratively showing the cross section of the patch according to one embodiment of the present description. The thickness occupied by the first drug layer is represented by h1, and the total thickness of the drug layer is represented by H. P' and P'' denotes the end point in contact with the through hole, respectively.

In one embodiment, the thickness (h1 of FIG. 2) of the first drug layer (20a) may be 50% or less, preferably 40% or less, of the total thickness (H of FIG. 2) of the drug layer, based on the longitudinal section (surface cutting the line connecting A-A' of FIG. 1) of the patch (1), and when having the above range, the release of the effective amount of the active ingredient may be achieved and the amount of the base or adhesive polymer remained after removal may be reduced.

The drug layer according to the present description may comprise an active ingredient and a base polymer, and the active ingredient may be stored inside and/or outside of the matrix formed by the base polymer. The drug layer may be provided in a dry matrix type, and may provide sufficient adhesive strength when connecting to a target site comprising moisture and the active ingredient may begin to be released. The dry matrix type may exhibit little or very low adhesive strength before exposed to moisture and then exhibit adhesive strength as the drug layer begins to hydrate due to exposure to moisture. The "active ingredient" is a component provided to achieve a desired effect of the patch according to the contents disclosed herein, and for example, it may be understood that the patch for tooth whitening has a component for tooth whitening as an active ingredient and the patch for relieving sensitive teeth has a component for relieving sensitive teeth as an active ingredient. The example of the active ingredient may comprise a component for tooth whitening, a component for preventing or improving sensitive teeth, a component for preventing or improving periodontitis, or a component for preventing or improving gingivitis. The component for tooth whitening may include peroxides, polyphosphate, enzymes, and chlorine bleach. The peroxide may be used by selecting from the group consisting of hydrogen peroxide, carbamide peroxide, calcium peroxide, sodium percarbonate, sodium perborate, tetrasodiumpyrophosphate peroxidate and a mixture thereof. The phosphate and enzyme are effective in removing major stains contained in the enamel adhesive layer. As the polyphosphate, one or more of tetrasodium pyrophosphate (TSPP), sodium acid pyrophosphate (SAPP), sodium hexametaphosphate (SHMP), sodium tripolyphosphate (STP), sodium potassium tripolyphosphate (SKTP), tetrapotassium pyrophosphate (TKPP) and ultraphosphate, acidic sodium meta-polyphosphate and acidic sodium polyphosphate may be used. In general, the polyphosphate is known to be effective in inhibiting tartar production or removing tartar as a tartar controlling agent in toothpaste. In addition, it is a good chelating agent of metal and therefore, it can effectively remove tooth stains produced by food or metal such as iron, calcium, magnesium, etc. in the working environment among tooth stains, thereby slightly contributing to improvement of the whitening effect. The chlorine bleach includes sodium chloride, sodium hypochlorite, and the like. Besides, papain, vitamin E and sodium bicarbonate, and the like may be used as a whitening agent. In another example, as the component for preventing or improving sensitive teeth or component for preventing a cavity, strontium chloride, calcium carbonate, sodium citrate, sodium fluoride, silica, hydroxyapatite, potassium nitrate, potassium phosphate, and the like may be used. In other example, the active ingredient may comprise a component for preventing a periodontal disease, and the periodontal disease clinically refers to the loss of teeth due to periodontitis, gingivitis and bleeding, formation of periodontal pockets and destruction of the alveolar bone, and the like. To prevent occurrence of periodontal disease, the drug layer may comprise bamboo salt, titrated extract of theunsaponifiable fraction of *Zea mays*, policresulen, tetracycline, chlorhexidine gluconate, cetylpyridium chloride, sanguinarine and triclosan, and the like, and may comprise herb medicine extract such as *magnolia, Centella asiatica*, chamomile, rhatany, myrrh, *morus* bark, black cohosh, green tea, licorice, *Scutellariae radix, Taraxacum platycarpum, Lonicera japonica*, and the like.

In addition to the active ingredient, the drug layer may comprise components that can be applied to a patch attaching to a common tooth or oral mucous membrane such as a wetting agent, a thickener, a bubble generating agent, an abrasive, and the like.

The drug layer may be eroded from the adhesive surface by moisture such as saliva or the like. The meaning of "may be eroded" used herein may be understood as a distorted shape compared to before exposure to moisture. It may be eroded by hydration, in which the polymer matrix chains are released by water or saliva. The base polymers constituting the drug layer are used in a sufficient amount to increase the efficacy by exerting the efficacy of the active ingredient or improving the stability of the active ingredient. However, in case of a patch that needs to be removed after use, when the polymer forming the drug layer is excessively hydrated, the base polymer remains on the tooth when it is removed after use of the patch on the tooth surface, and inconvenience of removing it separately may occur. Through one embodiment of the present disclosure, a drug layer is to be provided, in which some regions of the drug layer are separated by a reticular structure, thereby preventing excessive hydration or erosion of the drug layer and making movement or flow of the loaded active ingredient smooth.

The patch of the present disclosure may comprise a matrix type patch. The patch may be a dry type patch, in which there is no adhesive strength or strength is weak in a dry state, and the adhesive strength becomes higher by hydration with a small amount of water at a target site, and then the hydration causes to release the whitening agent. The active ingredient comprised in the drug layer is not released during storage or distribution or when touched by hand, but adhesion and release of the active ingredient are allowed as it is hydrated by moisture on the tooth surface or oral cavity. As the base polymer forming the drug layer, a polymer which may be hydrated or eroded by water or saliva may be used, and preferably, a water-soluble, water-swellable or water-dispersible polymer may be used. As the water-soluble, water-swellable or water-dispersible polymer, a polymer recognized in the art may be used without limitation, but considering characteristics of the target site (for example, wet environment, surface non-uniformity, etc.), any one or more selected from the group consisting of polyvinylpyrrolidone, carbomer, pullulan, carrageenan, sodium alginate, acrylate polymer or copolymer, water-soluble cellulose-based polymer, xanthan gum and polyvinyl alcohol which can generate strong adhesive strength to the target site and at the same time, release an active ingredient, when hydrated in the moist oral cavity, and most preferably, polyvinylpyrrolidone (PVP) may be comprised. In particular, the polyvinylpyrrolidone has excellent adhesive strength to a tooth or the oral mucosa and may be preferably used to maintain the stability of whitening components such as hydrogen peroxide. The polymer may be comprised in an amount of 20 to 50% by weight, preferably, 30 to 45% by weight, more preferably, 35 to 40% by weight based on the total weight of the patch after drying. When it is in the above content range, it is advantageous to achieve the object of the present disclosure. As its solvent, water, ethanol or a mixture thereof may be used. The drug layer may further comprise any one or more plasticizers selected from the group consisting of polypropylene glycol, glycerin, or polyethylene glycol, castor oil, PEG-60 hydrogenated castor oil, PEG-40 hydrogenated castor oil, and combination thereof, to provide sufficient flexibility. In addition, when a component for tooth whitening is comprised in the drug layer, a tooth whitening component stabilizer may be further comprised for the purpose of improving the aging stability of peroxide, and for example, EDTA or sodium citrate, or the like may be added. The active ingredient may be comprised in both the first drug layer (20a) and the second drug layer (20b), or present only in the second drug layer.

The adhesive surface of the drug layer may be optionally protected by a release liner. The adhesive surface is part of the drug layer, but it may be formed separately. The release liner may be removed before using the patch. As the release liner, paper, non-woven fabric, water-insoluble film (particularly, PET), or the like may be used, but not limited thereto.

Reticular Structure (10)

In one example, the patch (1) may comprise a reticular structure (10), and the reticular structure may be positioned preferably in the drug layer. By the reticular structure (10), the drug layer (20) may be divided into at least 2 or more layers.

The "reticular structure" according to the contents disclosed herein may be understood to mean a form having a weave that is entangled like a net, and may be used as a substitute for 'web', 'net', 'mesh' or the like.

In one example, by comprising the reticular structure (10) in the drug layer (20), the first drug layer (20a) may be present between the reticular structure (10) and the adhesive surface (21). In one embodiment, the first drug layer (20a) may show adhesiveness and the reticular structure may play a role in blocking adhesiveness of the second drug layer (20b), so removing the patch after use may leave little residue of the sticky drug layer on the tooth. The adhesiveness of the patch (1) may be achieved by the first drug layer (20a). In one embodiment, the characteristics of the first drug layer (20a) may provide an important meaning in achievement of the purpose of the present disclosure.

In one embodiment of the present disclosure, the patch (1) comprising the reticular structure (10) is provided, and the reticular structure may have an embo pattern (111a, 111b) and a through hole (112). The method for preparing the reticular structure as disclosed herein is not particularly limited, and it may be obtained by weaving one or more types of filaments, but it may be obtained by injection molding method using a pre-processed mold. When the reticular structure is obtained by weaving 2 or more filaments, 2 or more filaments cross each other and become thicker than the thickness of the single filament itself, and so it can play an embo role in itself, and therefore separate embo processing may not be applied.

The term used herein, "embo" is a term commonly used in the art, and it may be understood as referring to thicknesses of the portions different from each other in the reticular structure which is not uniform or a shape in which thicknesses are formed, based on the vertical section (A-A') of the patch, and a large number of embos may be included to form an embo pattern. In one embodiment, the embo may be formed in some areas of the filament, and preferably, it may be comprised in the filament connection. The meaning of that it may be comprised in the filament connection is forming an embo as the filament connection itself becomes thicker and has a convex structure due to the nature of the filament connection where 2 or more filaments overlap, or forming a convex structure through a separate treatment on the top of the filament connection, and the process by which the embo is made is not particularly limited. Due to the convex surface (111a) of the embo, the first drug layer (20a) may become thinner, or due to the concave surface (111b), it may become thicker. The concave surface (111b) is a long position drawn vertically to the reticular structure (10) with respect to the adhesive surface (21), and the convex surface (111a) is a short surface drawn up to the reticular structure (10) vertically with respect to the adhesive surface (21). As the amount of the polymer present in the first drug layer at the position of the convex surface is less or small, the adhesive strength to the tooth or oral cavity may be further weakened. In other words, the adhesive strength to the tooth or oral cavity of the patch constitutes the strong surface and weak surface based on the surface of the adhesive surface, so the removal of the patch may be easily carried out after completing the use of the patch.

By the embo pattern, the adhesive strength of the patch may be controlled, and the deviation of the adhesive strength can make the patch be removed more easily after use according to the position of the drug layer. The meaning of easily removing may include a meaning of neat removal without leaving excessive drug layer residues on the tooth.

The reticular structure (10) allows movement of an active ingredient, saliva, and the like, but comprises a through hole (112) in which the movement of the polymer is limited. The first drug layer and the second drug layer may contact through the through hole. The through hole may have a size of 0.01 to 0.5 mm$^2$, 0.015 to 0.4 mm$^2$, 0.018 to 0.38 mm$^2$, 0.02 to 0.35 mm$^2$, respectively. When it has the above size range, the movement of the active ingredient and moisture in the drug layer may be facilitated and the passage of the polymer in the second drug layer may be blocked.

The total area which the through hole (112) has may be an area of 10 to 60%, 12 to 55%, 13 to 50% based on the total area which one side of the reticular structure (10) has, when the reticular structure (10) is arranged horizontally with the adhesive surface (21). When the area of the through hole (112) is 10% or less based on the total area, it may be too fine to join the first drug layer (20a) and the second drug layer (20b), and when it is 60% or more, it may be difficult to show sufficient tensile strength when using. The number of the through hole (112) may be 100 to 800, 110 to 700, 120 to 600, 130 to 500, 140 to 400, 145 to 350 per unit area 1 cm$^2$ of the reticular structure surface, and when it has the above size range, the movement of the active ingredient and moisture in the drug layer may be facilitated and the passage of the polymer of the second drug layer may be blocked. The through hole having the above range makes the movement of hydrogen peroxide smoothly, and thereby may release an active ingredient distributed in the second drug layer (20b) to a target site and may also prevent excessive hydration of the base polymer in the second drug layer (20a) and block the movement of the polymer. As adhesiveness is exhibited by the first drug layer (20a) (preferably, polymer), the excessive amount of the adhesive polymer may be not used for attachment of the patch and therefore, even if the patch is removed after use, it may leave little residue on the tooth. For control of the adhesive strength and smooth movement of hydrogen peroxide, the position of the reticular structure may be considered, or the size of the through hole of the reticular structure or area occupied by the through hole may be considered.

The shape of the through hole is not limited. The shape is not particularly limited as long as saliva, an active ingredient and the like may move smoothly through the through hole and block the flow of the polymer.

Various embodiments of the reticular structure may be illustrated as follows.

Figure 3:
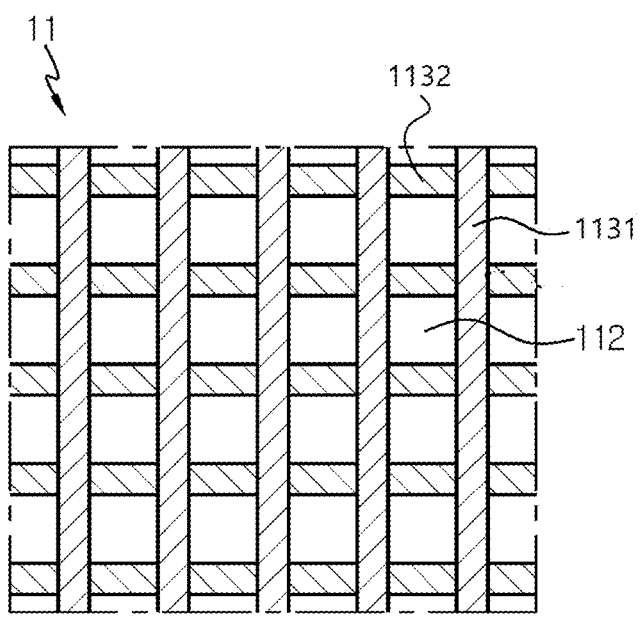
FIG. 3 to FIG. 5 are top plan views illustratively showing the reticular structure.
Figure 4:
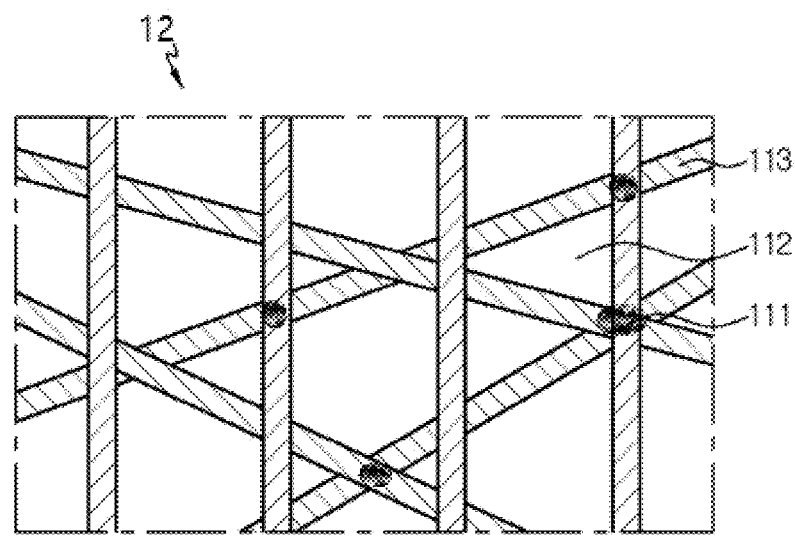
Figure 5:
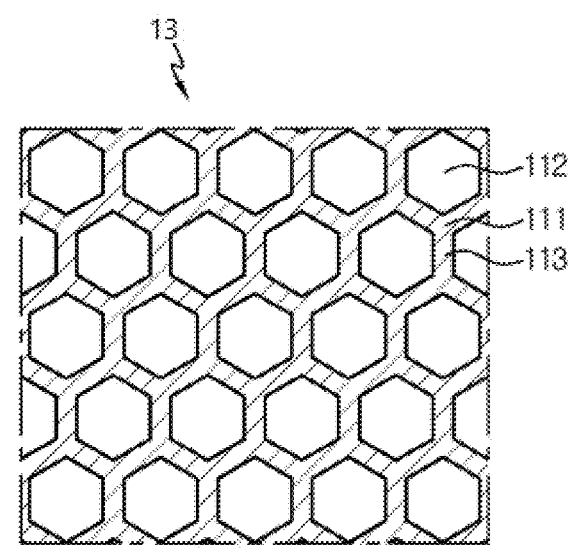
Figure 6:
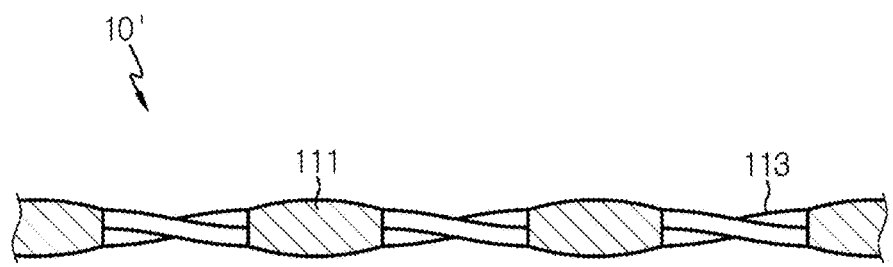
FIG. 6 illustratively schematizes the weave of two or more of filaments composing the reticular structure.

In one illustrative embodiment, as schematized in FIG. 3, using various strands of warp (1131) and weft (1132), the reticular structure (11) having a plurality of cross regions and a plurality of through holes (112) may be provided. The warp (1131) and weft (1132) may use the same type of filaments or different types of filaments. Through other embodiments, a reticular structure (12) in which filaments are arranged without a certain interval may be provided. As schematized in FIG. 4, a reticular structure (12) having a standardized through hole (112) may be provided. For example, one or more embos (11) may be comprised in a random region of the filament. As schematized in FIG. 5, a reticular structure (13) may be produced in a shape in which the filament (113) is connected or meets. For example, a reticular structure may be provided by a mold formed in a desired shape. In FIG. 3 to FIG. 5, as one embodiment, the part connecting the filament (113) of the reticular structure schematized refers to the filament connection, and is a part in which the filaments are connected or meet or cross each other, and in order to achieve the purpose of the present description, an embo having a convex surface (111*a*) may be comprised in the part in which the filaments are connected. In the filament connection, at least 2 or more filaments may be connected, meet or cross each other, and 2 or 3 or more filaments may meet or cross. For example, FIG. 6 schematizes weaving of 2 or more filaments constituting a reticular structure, and schematizes and illustratively shows a state in which the filament connection in which 2 or more filaments (113) are overlapped to form an embo (111) pattern. The material of the reticular structure may comprise any one or more polymer filaments selected from the group consisting of acrylic, polyester, nylon, polypropylene, polyethylene, polybutylene terephthalate, ethylene vinyl acetate, and combination thereof, and a water-insoluble material may be used without limitation, and preferably, may comprise a polyethylene filament. The polyethylene (PE) reticular structure may provide appropriate tensile strength which can prevent breakage of the backing layer (particularly, ethyl cellulose backing layer), and may help to maintain a shape as it is not dissolved by saliva in the oral cavity.

The term used to describe the reticular structure, "filament" may be used in a meaning that encompasses all meanings one side of the shape when a number of thin, straight synthetic plastics are connected to form a thread-like structure, or to form a shape of a honeycomb, square, triangle, and the like.

The reticular structure may have unevenness including a convex surface (111*a*) and a concave surface (111*b*). Due to this, the first drug layer (20*a*) may have relatively thin and thick regions in which the thickness is not uniform. As a small amount of the adhesive polymer is present in the thin layer compared to the thick layer in the first drug layer (20*a*) and thus the adhesive strength is weakly provided, and therefore, a smaller amount of tooth residues may be left after use of the patch.

In one embodiment, the reticular structure may have a thickness of 50 to 300 μm, preferably, 60 to 250 μm, preferably, 80 to 200 μm. When having the above thickness range, it may be stably positioned in the drug layer and may be neatly removed with the backing layer when detaching the patch.

Backing Layer (30)

The patch (1) according to the contents of the present description may further comprise a backing layer (30) on the other side of the adhesive surface (21) of the drug layer (20). The "backing layer" used herein means a layer playing a role in preventing the drug layer from connecting to other site in the oral cavity than the tooth or target site. Preferably, the backing layer has water-impermeability or water-insolubility.

In other example of the present disclosure, in case of a patch having a drug layer eroded by water or saliva, etc., it is recognized that a problem that a drug layer and a backing layer are separated occurs, and a patch capable of improving it is to be provided. The present inventors have confirmed that a problem that the drug layer and backing layer are separated may occur as there is no binding ability of interaction between the backing layer and drug layer. The backing layer according to the present description may comprise any one or more selected from a water-insoluble polymer having a hydrophilic functional group of a hydroxyl group or a carboxyl group, a thermoplastic or a mixture thereof. The water-insoluble polymer having a hydrophilic functional group of a hydroxyl group or a carboxyl group may include one or more polymer selected from the group consisting of ethyl cellulose, cellulose acetate, polymethylmethacrylate copolymer, acetate-polyvinylpyrrolidone copolymer, and combination thereof, and preferably, may include ethyl cellulose. The backing layer using ethyl cellulose as a base polymer may reduce or prevent a phenomenon of separating from the drug layer and therefore may increase the binding ability with the drug layer. The thermoplastic may include one or more selected from the group consisting of polyethylene, polyethylene terephthalate, polyvinyl chloride, polyvinylidene chloride, polystyrene, polypropylene, and combination thereof, and preferably, the thermoplastic may include polyethylene. In particular, the thermoplastic, particularly, polyethylene may have an excellent effect in preventing separation of the drug layer and the backing layer when a reticular structure having an embo pattern is comprised.

In one embodiment, the backing layer of the patch according to the present description may comprise the polymer in an amount of 60 to 90% by weight based on the total weight of the backing layer on the basis of the dried patch, considering prevention of the backing layer and drug layer and/or tensile strength of the backing layer, and preferably, it may comprise 65 to 80% by weight.

Preferably, ethyl cellulose may be comprised as a water-insoluble polymer. The ethyl cellulose has weak tensile strength and so in case that the drug layer is hydrated and has adhesive strength, a problem that it is broken or torn when removed after use occurs, but when it is used for the drug layer equipped with the reticular structure of the present disclosure, the tensile strength of the backing layer may be supplemented and thereby, a problem that the patch is torn or broken may be prevented. The patch, backing layer and reticular structure of the present disclosure is preferably have tensile strength of about 300 gf to 2000 gf, about 400 to 1500 gf, considering the adhesive strength between the tooth and the first drug layer. When having the above range, a phenomenon that it is broken or separation of the reticular structure and backing layer are separated when removing the tooth patch may be prevented.

Preferably, the backing layer may comprise a surfactant, a plasticizer, a wetting agent and the like, in addition to the water-insoluble polymer, and a component used in preparing a backing layer in the art preparing a tooth adhesive patch may be used without limitation. Specifically, the surfactant may be any one or more selected from the group consisting of SPAN20, SPAN40, SPAN60 and SPAN80, and preferably, SPAN80 may be comprised for the purpose of the present disclosure. The content of the surfactant may be comprised in an amount of 5 to 20% by weight based on the total dry weight of the backing layer. As the plasticizer, castor oil may be comprised for the purpose of the present disclosure. The content of the plasticizer may be comprised in an amount of 5 to 20% by weight based on the total dry weight of the backing layer. The backing layer may further comprise a plasticizer as same as the drug layer. As a solvent, mostly, water, ethanol alone or a mixture thereof, and other inorganic solvents, for example, ethyl acetate, methylene chloride, isopropyl alcohol, acetonitrile alone or a mixture thereof may be used by adjusting the ratio.

The tooth adhesive patch of the present disclosure may further equip an additional layer in the outer periphery of the backing layer or between the drug layer and backing layer optionally, depending on the purpose, in addition to the drug layer and backing layer.

Kit for Tooth Whitening

One example of the present disclosure provides a kit comprising the patch according to the present description, and for example, a kit for whitening tooth or teeth comprising the patch comprising a component for whitening tooth or teeth according to the present description, a kit for relieving, preventing or inhibiting sensitive tooth or teeth comprising the patch comprising a component for relieving, preventing or inhibiting sensitive tooth or teeth, and a kit for relieving, preventing or inhibiting halitosis comprising the patch comprising a component for removing, relieving or preventing halitosis may be provided.

The kit may comprise an instruction manual, guidebook, order or the like, which may provide instructions for application, use, spreading, attachment and the like of the patch according to the present description. Additionally, the kit may comprise a tool for attachment capable of attaching the patch (for example, tongs, tweezer), or tool for removing moisture on the tooth or mucous membrane surface before use (for example, tissue, gauze, etc.) or the like. In the instruction manual, guidebook, order and the like, the method for using the present patch may be included. As one of the methods for using the patch, information about time to be removed after attachment of the patch may be included. For example, after attaching the patch to the target site, in 3 minutes to 12 hours, more preferably, 5 minutes to 3 hours, further more preferably, 10 minutes to 90 minutes, the patch may be removed by holding the backing layer. In addition, the kit may preferably comprise a kit for whitening tooth or teeth, and helpful information for evaluating a whitening effect achieved by the method and patch of the present description and the like (for example, diagram, etc.) may be comprised.

The kit for whitening tooth or teeth according to one example of the present disclosure may further comprise a composition for activating whitening efficacy by promoting degradation of peroxide compounds contained in the patch. Because the patch for tooth whitening comprises a base polymer for stabilization of peroxide compounds such as hydrogen peroxide, more time may be required for hydrogen peroxide to act. Accordingly, the composition for activating whitening may comprise a metal ion for activating a hydrogen peroxide component, for example, iron chloride component, copper ion-containing compound, and the like. The component for activating hydrogen peroxide is commonly known in the art. In addition, as hydrogen peroxide is activated in a basic state, the pH of the composition for activating whitening may be basic. The composition for activating whitening may induce gum or oral cavity stimulation due to excessive activation of hydrogen peroxide, and therefore the kit for tooth whitening may further comprise a stimulus reliever in any one of the patch or composition for activating whitening or as a separate composition. As the component for the stimulus reliever, a component commonly known in the art may be comprised.

Method for Using the Patch

According to one example of the present description, present disclosure, an intended effect may be obtained by releasing an active ingredient in the patch to a target site. The intended effect may be understood as an intended effect of the active ingredient. For example, a method for whitening a tooth or teeth using the patch or kit comprising the patch is provided. In one example, preparing the patch according to the present description, attaching the patch to a target site such as a tooth, teeth or oral cavity, and removing the patch from the target site after a certain period of time may be comprised. The patch may be removed by holding and detaching the backing layer, for example, after attaching the patch to the target site, in 3 minutes to 12 hours, more preferably, 5 minutes to 3 hours, further more preferably, 10 minutes to 90 minutes. In the method for whitening tooth or teeth according to the present description, a tooth whitening component evenly distributed in the drug layer may pass through the through hole, move to the tooth surface, and whiten the tooth. Specifically, when the first drug layer (20a) is hydrated by saliva or moisture, the saliva or moisture passes through a through hole (112) in the reticular structure and is delivered to the second drug layer (20b) and thereby, an active ingredient (preferably, hydrogen peroxide) in the second drug layer flows into the tooth surface by passing through the channel formed between the swelled polymers, so that the active ingredient may be delivered to the tooth or teeth. However, the present tooth whitening method is not limited to this theory, and any tooth whitening method using the patch according to the present description may be included to the scope of the present disclosure without limitation. The tooth whitening method according to the present description may have an excellent tooth whitening effect, and when the patch is removed after use, almost residue remained on the tooth are neatly removed.

Method for Preparing the Patch

One embodiment provides a preparation method of a patch comprising a reticular structure in a drug layer. The reticular structure may divide the drug layer into a first drug layer and a second drug layer.

One embodiment may comprise:

(S1) preparing a drug layer preparation solution comprising a water-soluble, water-swellable or water-dispersible polymer and an active ingredient, (S2) drying a certain amount of the drug layer preparation solution in a film form to form a first drug layer, (S3) laminating or applying a reticular structure, and then applying a certain or remained amount of the drug layer preparation solution to the first drug layer and drying to form a second drug layer; and (S4) locating a backing layer on the second drug layer, and optionally drying.

If necessary, after the above step (S4), further drying the patch may be comprised.

The drug layer preparation solution may be provided as a viscous gel. The drug layer preparation solution may be dried after applied on the film base, for example release liner. The surface in contact with the film base may be an adhesive surface of the drug layer.

The drying may be carried out at a temperature of 40 to 60° C., or preferably 45 to 55° C.

In the dried patch, the drying time may be determined by the desired remaining content of the solvent (preferably, water) in the patch after drying. In addition, drying is carried out during a previously determined time so that the water content in the drug layer of the patch become 5~50%, preferably 15~45%, more preferably 25~42%, at room temperature after drying. If the solvent is water, the content of water may be determined by Karl-fisher method. The reticular structure may divide the drug layer into the first drug layer and the second drug layer, and it may be positioned so that the thickness of the first drug layer has a thickness of about 5 to 50% of the total thickness of the drug layer based on the longitudinal section of the dried patch.

The backing layer may be positioned by applying and drying a backing layer preparation solution containing a water-insoluble polymer. As other example, the backing layer may be formed by attaching a water-insoluble film formed previously.

The patch may be produced so that the cross sectional area of the reticular structure and backing layer is broader than the cross sectional area of the drug layer. In this patch, the backing layer and reticular structure may be connected at the left and right ends without the drug layer. As the reticular structure and backing layer come into contact with each other, when the patch is removed after use, it may be prevented that only the backing layer is detached and the reticular structure is remaining in the tooth.

EXAMPLES

Hereinafter, examples, etc. will be described in detail to aid in understanding the present disclosure. However, examples according to the present disclosure may be modified in various different forms and the scope of the present disclosure should not be construed as being limited to the following examples. The examples of the present disclosure are provided to more completely explain the present disclosure to those with average knowledge in the field to which the present disclosure belongs.

As used herein, "about" may be understood as an extended range to ±10 of the stated value. For example, about 10% may include 9 to 11%, and may include decimals included in the above range. In addition, for example, about 1 cm may include 0.9 to 1.1 cm and may include up to decimals included in the above range.

[Production of a Patch Equipped with a Reticular Structure]

A patch for whitening a tooth or teeth comprising a drug layer and a backing layer according to one embodiment of the present disclosure was prepared with the composition of Table 1 below.

After preparing a gel composition for preparing the drug layer and a gel composition for preparing the backing layer with the composition of Table 1 below, the gel composition for preparing the drug layer was spread on PET (release liner) in the thickness of 70 um and then dried at the temperature of 50° C. for 10 minutes. After placing a reticular structure on the dried drug layer, the drug layer was coated once more in the thickness of 180 um including the thickness of the reticular structure, and dried at the temperature of 50° C. for 20 minutes, and the backing layer was coated in the thickness of 20 um and dried at the temperature of 50° C. for 20 minutes. Then, a patch was produced by additionally drying at 105° C. for 10 minutes so that the dried content was to be 15%.

The reticular structure of Example 1 was the product of H526 from SWM Company and the reticular structure of Comparative example 2 was the product of X540NAT from SWM company.

TABLE 1

| Patch having an ethyl cellulose (EC) backing layer | | | | | |
|---|---|---|---|---|---|
| Drug layer | Content | Function | Backing layer | Content | Function |
| Hydrogen peroxide | 10.0% | Active ingredient | Ethyl cellulose | 20% | Film former |
| PEG300 | 10.0% | Wetting agent | Castor oil | 5% | Plasticizer |
| Povidone | 20.0% | Film former | Glycerin | 5% | Plasticizer |
| Carbomer | 1.0% | Thickener | SPAN80 | 5% | Plasticizer |
| Sodium triphosphate | 0.1% | pH adjusting agent | Ethanol, etc. | To 100% | |
| Phosphate | 0.1% | pH adjusting agent | | | |
| Sodium saccharin hydrate | 0.1% | Sweetener | | | |
| Flavoring agent | 1.0% | Flavoring | | | |
| Water, etc. | To 100% | | | | |

[Evaluation of Delamination and Tensile Strength of Backing Layer Depending on the Backing Layer Material]

In order to compare with the patch produced by using the composition of Table 1, the patch produced by using the composition of Table 2 below was prepared by applying a polyethylene film, instead of ethyl cellulose, without a reticular structure in the second drug layer. The thickness of the drug layer of the prepared patch was 180 um including the reticular structure and the thickness of the backing layer was 20 um and thus the total thickness was 200 um.

TABLE 2

| Patch having a polyethylene (PE) backing layer | | | | | |
|---|---|---|---|---|---|
| Drug layer | Content | Function | Backing layer | Content | Function |
| Hydrogen peroxide | 10.0% | Active ingredient | Polyethylene | 20% | Film former |
| PEG300 | 10.0% | Wetting agent | Castor oil | 5% | Plasticizer |
| Povidone | 20.0% | Film former | Glycerin | 5% | Plasticizer |

TABLE 2-continued

Patch having a polyethylene (PE) backing layer

| Drug layer | Content | Function | Backing layer | Content | Function |
|---|---|---|---|---|---|
| Carbomer | 1.0% | Thickener | SPAN80 | 5% | Plasticizer |
| Sodium triphosphate | 0.1% | pH adjusting agent | Ethanol, etc. | To 100% | |
| Phosphate | 0.1% | pH adjusting agent | | | |
| Sodium saccharin hydrate | 0.1% | Sweetener | | | |
| Flavoring agent | 1.0% | Flavoring | | | |
| Water, etc. | To 100% | | | | |

1. Delamination of the Backing Layer at High Temperature

Figure 7:
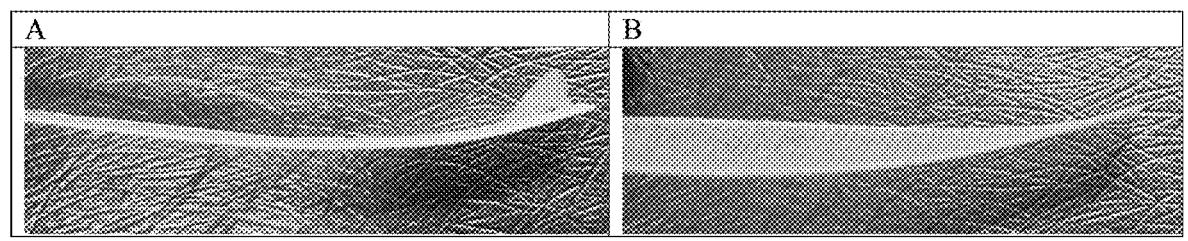
FIG. 7 is a comparative photograph confirming the phenomenon that the backing layer is separated in the patch during high temperature aging. The left (A) is the result of confirming the patch having the composition of Table 1 and the right (B) is the result of confirming the patch having the composition of Table 2, after leaving it in an oven at 60° C. for 24 hours.

A patch having a PE backing layer without a reticular structure (Patch (A)) and a patch having an EC backing layer with a reticular structure (Patch (B)) were produced (1 cm in the width and 6 cm in the length), and left in an oven at 60° C. for 24 hours, and then delamination of the backing layer was confirmed. The result is shown in FIG. 7. As shown in FIG. 7, Patch (B) had excellent stability even at a high temperature and had no separation between the drug layer and backing layer.

2-1. Change in Tensile Strength with or without a Reticular Structure

Used Equipment: TA/TX Analyzer

Figure 8:
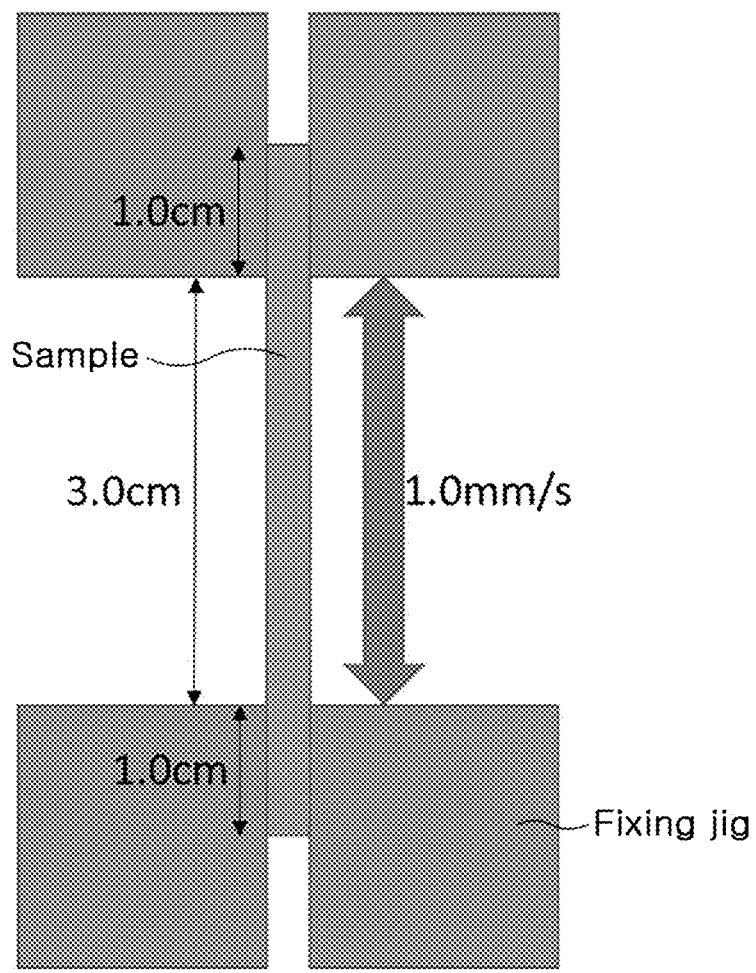
FIG. 8 shows the method for measuring the tensile strength.

Experimental method: The experimental method may refer to FIG. 8. The samples was cut into a certain size (1.0×5.0 cm) and fixed the position of 1.0 cm apart from each end to the fixing jig so that only 3.0 cm comes out. The tensile strength was measured by pulling 60.0 mm (extending by double of the original length) at the test speed of 1.0 mm/s.

Figure 9:
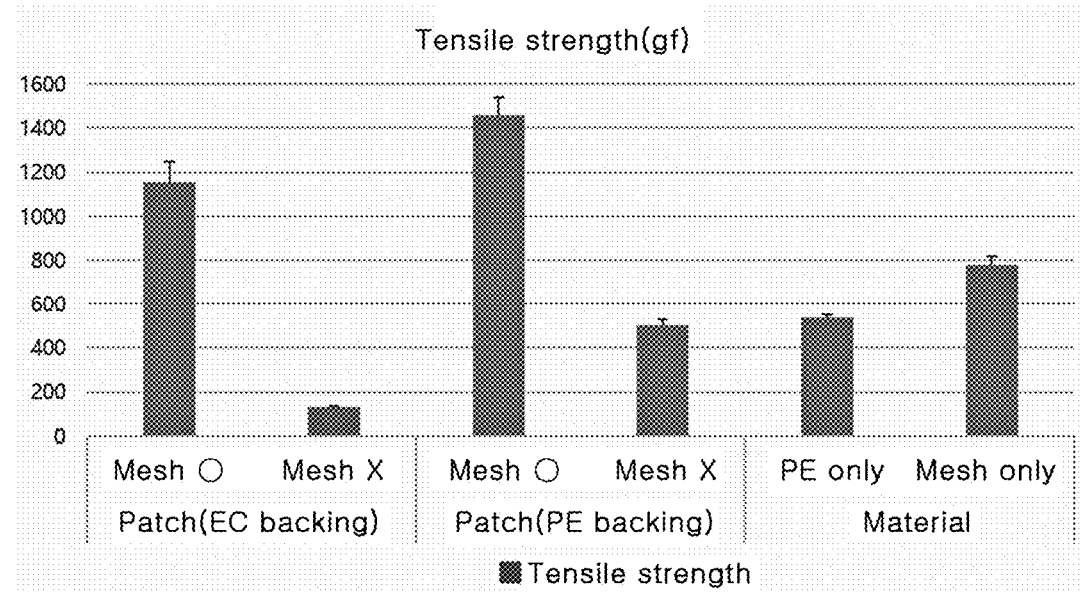
FIG. 9 is the result of evaluating the tensile strength.

The estimation result is shown in FIG. 9.

The tensile strength of the reticular structure without the polyethylene backing layer was 1000 gf or more. The tooth adhesive strength of the drug layer was about 350 gf (adhesive strength that measures the force when removing hydroxyapatite disc having 1 cm diameter after pressing it with 100 gf for 10 seconds). In order to smoothly remove the patch from the tooth, the tensile strength of the patch must be 350 gf or more, which is more than the adhesive strength between the drug layer in the patch and the tooth. When the reticular structure is comprised in the drug layer and ethyl cellulose is comprised in the backing layer, the tensile strength was twice or more higher than the adhesive strength between drug layer and the tooth, meaning smooth removal is allowable. In addition, Patch (B) with the reticular structure had a greater tensile strength than the tensile strength of the patch having the PE backing layer.

Therefore, these results show that the patch with the EC backing layer and reticular structure does not cause delamination or separation between the backing layer and the drug layer at removal after use because of its excellent tensile strength.

Figure 10:
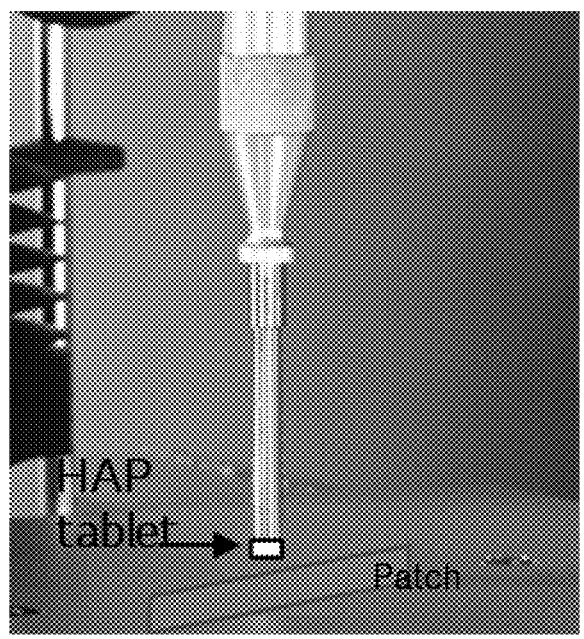
FIG. 10 shows the experimental method for removing the patch.

2-2. Breakage of the Patch (without EC Backing & Mesh) Due to the Difference in the Adhesive Strength and Tensile Strength of the Patch Used Equipment: TA/TX Analyzer Experimental method: The device for the experiment was shown in FIG. 10. The experiment was performed with the patch produced with the composition of Table 1. The HAP tablet having 1.0 cm of diameter was attached at the end of the jig. After the patch was turned over and fixed to the bottom, 20 μl of water was dropped in a circle of 1.0 cm diameter to wet the patch, and then the patch was pressed with a force of 100 gf for 10 seconds, and then the force upon removal was measured.

Experimental result: The force between the adhesive surface of the patch and the HAP tablet was 341.7±18.0 gf, and the adhesive force was twice and more than the tensile strength (133.2±2.34 gf) of the patch having EC backing layer without reticular structure. It means that breakage can occur at removal. However, when the reticular structure is inserted in the drug layer, the tensile strength of the patch is increased to 1152.7±95.12 gf, so that the patch does not cause breakage at removal, resulting in increasing the feeling of use during removal.

3. Stability at High Temperature (50° C.) (PE Delamination)

Delamination of the backing layer at a high temperature was evaluated according to the modification of the composition of the drug layer. The composition of the drug layer as evaluated was represented by Compositions 1 to 5, respectively. A PE reticular structure was inserted in the drug layer. However, as the result, regardless of the composition, separation occurred in case of using the PE backing layer, but in case of using the ethyl cellulose backing layer, separation or delamination did not occur.

The patches of Compositions 1 to 5 having the EC backing layer were described as Examples 1, 2, 3, 4 and 5 in Table 4, and the patches of Compositions 1 to 5 having the PE backing layer were described as Examples 1-2, 2-2, 3-2, 4-2 and 5-2 in Table. The method for preparing the patch was same as described above.

TABLE 3

| | Composition 1 | Composition 2 | Composition 3 | Composition 4 | Composition 5 |
|---|---|---|---|---|---|
| Hydrogen peroxide | 10.0 | 10.0 | 10.0 | 10.0 | 10.0 |
| Glycerin | | 10.0 | | | |
| PEG300 | 10.0 | | | | 10.0 |
| HCO40 | | | 10.0 | | |

TABLE 3-continued

|  | Composition 1 | Composition 2 | Composition 3 | Composition 4 | Composition 5 |
|---|---|---|---|---|---|
| SPAN80 |  |  |  | 10.0 |  |
| Povidone | 20.0 | 20.0 | 21.0 | 21.0 | 16.0 |
| Carbomer | 1.0 | 1.0 |  |  |  |
| Pullulan |  |  |  |  | 5.0 |
| Sodium saccharin | 0.1 | 0.1 | 0.1 | 0.1 | 0.1 |
| Flavoring agent | 1.0 | 1.0 | 1.0 | 1.0 | 1.0 |
| Phosphate | 0.1 | 0.1 | 0.1 | 0.1 | 0.1 |
| Sodium triphosphate | 0.1 | 0.1 | 0.1 | 0.1 | 0.1 |
| Purified water | to 100 | to 100 | to 100 | to 100 | to 100 |

TABLE 4

○: No delaminated or separated Δ: Slightly separated X: Completely separated

| 50° C. Aging | 3 Day | 5 Day | 1 week | 2 week | 3 week | 4 week |
|---|---|---|---|---|---|---|
| Example 1 | ○ | ○ | ○ | ○ | ○ | ○ |
| Example 1-2 | ○ | Δ | X | X | X | X |
| Example 2 | ○ | ○ | ○ | ○ | ○ | ○ |
| Example 2-2 | Δ | Δ | X | X | X | X |
| Example 3 | ○ | ○ | ○ | ○ | ○ | ○ |
| Example 3-2 | ○ | X | X | X | X | X |
| Example 4 | ○ | ○ | ○ | ○ | ○ | ○ |
| Example 4-2 | ○ | ○ | Δ | X | X | X |
| Example 5 | ○ | ○ | ○ | ○ | ○ | ○ |
| Example 5-2 | ○ | Δ | X | X | X | X |

X represents separation is observed immediately.
Δ denotes separation occurs when the patch is held for use or when it is removed from PET (when a physical external force is applied).
○ represents no delamination or separation between the backing layer and the drug layer is observed.

The results in the Table 4 show that delamination or separation between the backing layer and the drug layer may occur depending on the material of backing layer.

4. Cost Reduction Effect Through Bulk Packaging

The backing layer of PE film may cause adhesion between and contamination of patches due to delamination or separation of the PE film during bulk packaging, but when an EC backing layer is used, there is no problem of delamination or separation, so bulk packaging is allowable, thereby increasing productability.

5. Evaluation on Residue

Experimental method: Each patch was pressed on a HAP disc (1.0 cm in diameter) with a 200 g weight for 10 seconds, and left for 1 hour, and then the patch was removed, and then stained with KI to measure the residual amount of the patch remaining on the HAP disc.

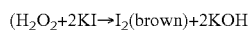

$(H_2O_2 + 2KI \rightarrow I_2(brown) + 2KOH)$  Reaction formula:)

Experimental sample: the patch not using the reticular structure but having the composition of Example 1 in Table 3 (Existing) and the patch comprising a reticular structure and having the composition of Example 1 (Improved)

Figure 11:
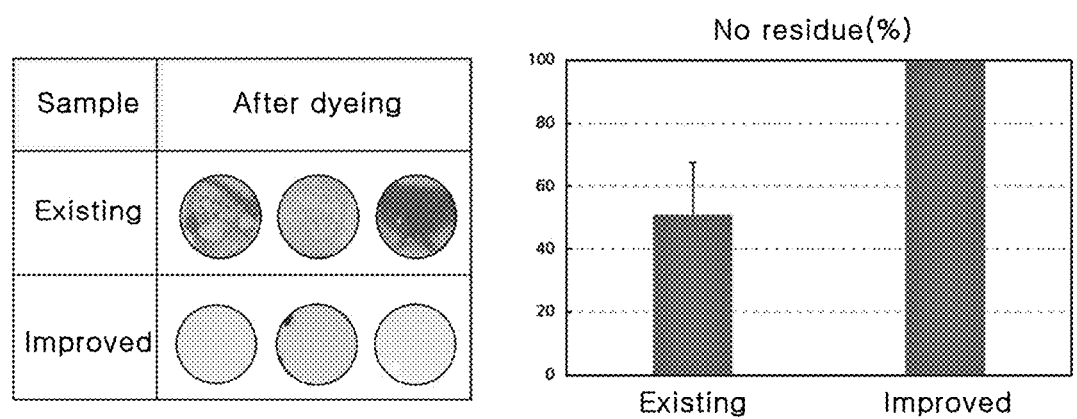
FIG. 11 is the result of confirming the remaining amount of the drug layer.

Experimental results: in case of the patches according to the invention having improvement of the structure, the reduced residue remain on the HAP disc, it means that the patches can be neatly removed. The results as repeated 3 times were shown in FIG. 11. Referring to FIG. 11, the patches not comprising reticular structure (Existing) remained a large amount of residues on the tooth surface due to excessive hydration of the drug layer. However, the patches comprising reticular structure (Improved) remained no or reduced residue on the tooth surface (reached almost 100%), it means that it may be neatly removed from the tooth surface. As for the degree of no residue, the ratio of the stained area per total area was calculated. Using image J program, the total area and the stained area were calculated in pixel units.

[Production of a Patch Having an Ethylcellouse Backing Layer and a Drug Layer Comprising a Reticular Structure]

The patches having reticular structure in the drug layer and the backing layer of ethyl cellulose was produced.

Figure 12:
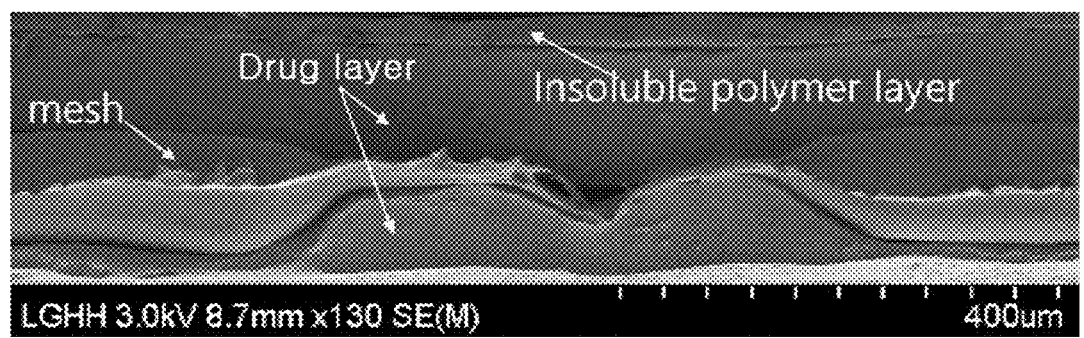
FIG. 12 shows the cross-sectional SEM photograph of the patch according to one example of the present disclosure.

FIG. 12 is the SEM photograph showing the cross-section of the patch according to the Example 1. The drug layer is present between the reticular structure in the drug layer and the backing layer (EC), and the drug layer is also present between the adhesive surface of the drug layer and the reticular structure.

In addition, the thickness of the drug layers between the reticular structure and adhesive surface was different each other along the convex surface of the reticular structure. The drug layer applied on the concave surface of the reticular structure is thick and the drug layer attached to the tooth on the convex surface is thin or not present. Due to this, the convex surface of the reticular structure provides weak adhesive strength to the tooth (thin drug layer) and the concave surface of the reticular structure provides relatively strong adhesive strength to the tooth (thick drug layer), and it means that the patch can be removed more easily.

Figure 13:
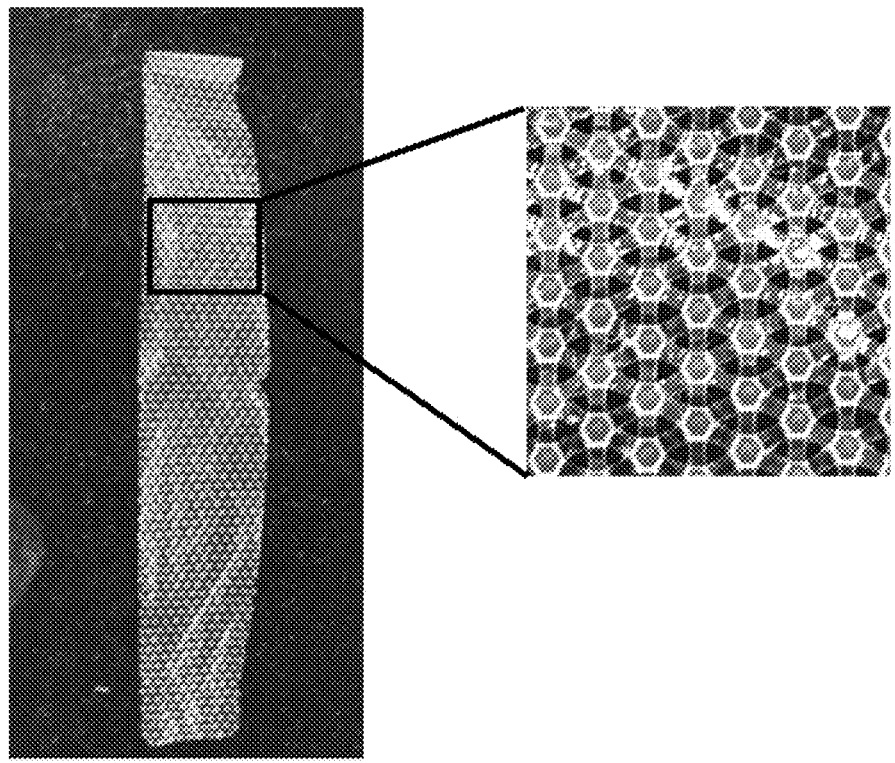
FIG. 13 is the photograph of enlarging the whole and enlarged view of the reticular structure according to the present description.

FIG. 13 is a photograph showing the reticular structure produced according to one example. On the right, the enlarged view of the reticular structure is shown. The reticular structure has a plurality of through holes and the embo pattern having convex surface is shown in the portion where the filaments cross each other. However, the photograph of FIG. 13 is only an example showing the reticular structure according to the present description, and the scope cannot be limited to this photograph.

The following is results evaluating the residue and the released amount of hydrogen peroxide according to the position of the reticular structure in drug layer. As the backing layer, ethyl cellulose is used.

1. Residue Evaluation According to the Position of the Reticular Structure in the Drug Layer In the present experiment, each patch was pressed on a HAP disc (1.0 cm in diameter) with a 200 g weight for 10 seconds, and left for 1 hour, and then stained with KI to measure the residual amount of the patch remaining on the HAP disc. (Reaction formula:$H_2O_2 + 2KI \rightarrow I_2$(Brown)+ 2KOH)

The experimental samples are shown in Table 5 below. The composition of the patches of Examples 6-8 and Comparative examples 1-2 below is same with that of Example 1.

TABLE 5

| | Sample | | | |
|---|---|---|---|---|
| | Example 6 | Example 7 | Example 8 | Comparative example 1 |
| Thickness of the first drug layer (μm) | 92 | 113 | 127 | 159 |
| Ratio of the thickness of the first drug layer to the thickness of the total drug layer | 34% | 42% | 47% | 59% |
| No residue (%) | 99.8 ± 0.3 | 99.7 ± 0.2 | 75.0 ± 1.9 | 50.1 ± 0.9 |

The reticular structure was placed in the drug layer so that each sample patches had the thickness of the first drug layer as shown in Table 5 above. The total thickness of the drug layer was about 270 μm. The total drying time of the drug layer was 40 minutes, and the drying time was appropriately allocated according to the coating thickness of the first drug layer and the applied thickness of the second drug layer. Other matters for manufacturing were same as previously described.

Figure 14:
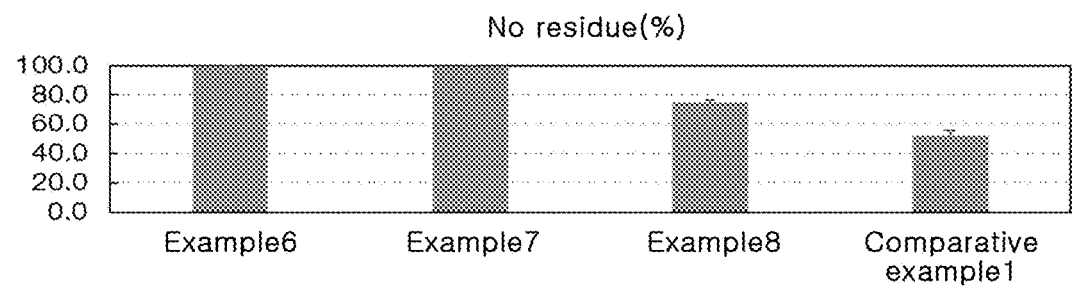
FIG. 14 is the result of confirming the remaining amount of the drug layer.

The result was shown in FIG. 14. As shown in in FIG. 14, there are significantly lesser residues on the teeth surface when the reticular structure is placed closer to the adhesive surface.

The residue evaluation was carried out in the same manner as previously described.

2. Evaluation of the Released Amount of Hydrogen Peroxide According to the Position of the Reticular Structure and the Total Area of the Through Hole The present was to evaluate the released amount of hydrogen peroxide by varying the position of the reticular structure in the drug layer and the total area of the through hole. The total area (per unit area of 1 cm$^2$) of the through hole of the Comparative example 2 is has approximately 1.9 times larger than that of Example 1.

After fixing the patch of Table 6 below on the bottom of the beaker with double-sided tape so that the drug layer faces the top, 50 ml of purified water was poured and left for 30 minutes, and then purified water was taken again in a separate beaker, and then the dissolved hydrogen peroxide content was measured and then calculated the released amount of hydrogen peroxide compared to the initial value. The total thickness of the drug layer was about 270 μm.

TABLE 6

| | Sample | | | | |
|---|---|---|---|---|---|
| | Example 6 | Comparative example 2 | Example 7 | Example 8 | Comparative example 1 |
| Thickness of the first drug layer (μm) | 92 | 92 | 113 | 127 | 159 |
| Ratio of the thickness of the first drug layer to the thickness of the total drug layer | 34% | 34% | 42% | 47% | 59% |
| Released amount of H$_2$O$_2$ (%) | 90.9 ± 0.8 | 90.12 ± 2.1 | 91.35 ± 0.8 | 90.5 ± 0.5 | 90.6 ± 0.1 |

Figure 15:
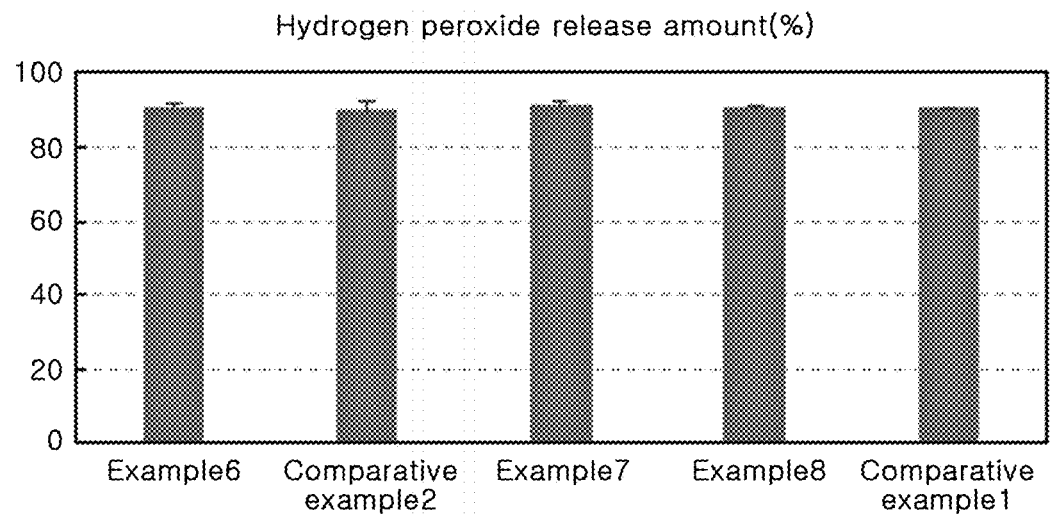
FIG. 15 is the result of confirming the hydrogen peroxide release amount.
Figure 16:
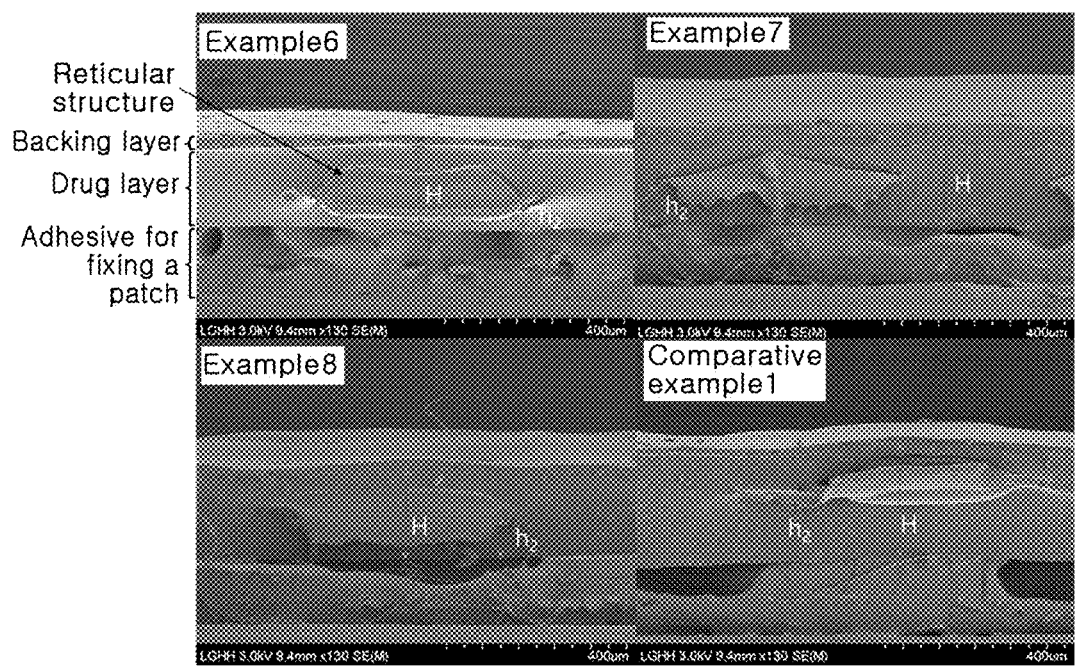
FIG. 16 shows the result of photographing the cross-sections of the patches of Examples 6 to 8 and Comparative example 1 as SEM photographs.

As shown in the Table 6 and FIG. 15, there is almost no difference in the released amount of hydrogen peroxide, despite the different positions of the reticular structure. Accordingly, the patch according to the present description can provide a patch having an excellent tooth whitening effect while the reduced amount of residue is remained on the tooth surface.

DESCRIPTION OF THE SYMBOLS

1: Patch
10: Reticular structure
11-13: Preparative example of various reticular structures
  111: Embo
    111*a*: Convex surface of embo
    111*b*: Concave surface of embo
  112: Through hole of reticular structure
  113: Filament
    1131: Warp
    1132: Weft
20: Drug layer
  20*a*: First drug layer
  20*b*: Second drug layer
  21: Adhesive surface
30: Backing layer
H: Total thickness occupied by the drug layer in the patch
h1: Thickness of the first drug layer

What is claimed is:

1. A patch for applying to a tooth or oral mucosa, comprising a drug layer having an adhesive surface and a backing layer laminated to the drug layer,
wherein the drug layer includes at least one reticular structure which divides the drug layer into multiple sections.

2. The patch according to claim 1, wherein the drug layer comprises two sections of a first drug layer and a second drug layer, wherein the first drug layer is between the adhesive surface and the reticular structure, and the second drug layer is between the first drug layer and the backing layer, and wherein the first drug layer has a thickness of 5 to 50% of the thickness of the total drug layer.

3. The patch according to claim 1, wherein the reticular structure comprises a through hole and an embo pattern, and the embo pattern has a convex portion and a concave portion, the convex portion being formed in the direction of the adhesive surface.

4. The patch according to claim 3, wherein the reticular structure has an embo pattern in a filament connection in which at least two filaments meet or cross, and a through hole formed between the filament connections through which the active ingredient passes.

5. The patch according to claim 3, wherein the through hole has an area of 10 to 60% relative to the total area of the reticular structure which is horizontal to the adhesive surface of the drug layer.

6. The patch according to claim 4, wherein the filament connection is formed by two filaments.

7. The patch according to claim 4, wherein the filament connection is formed by three filaments.

8. The patch according to claim 4, wherein the filaments forming the reticular structure are spaced apart from 30 to 500% of the thickness of the filament.

9. The patch according to claim 3, wherein the through hole in the reticular structure has an area of 0.01 to 0.5 mm$^2$ per one hole.

10. The patch according to claim 3, wherein the number of the through holes in the reticular structure are 100 to 800 per 1 cm$^2$ of unit area of the surface of the reticular structure.

11. The patch according to claim 1, which releases an active ingredient from the drug layer,
wherein the drug layer comprises a water-soluble, water-swellable or water-dispersed polymer, and is eroded by saliva or moisture to attach to a target site, and the adhesion is achieved by erosion of the first drug layer.

12. The patch according to claim 11, wherein the polymer is selected from the group consisting of polyvinyl pyrrolidone, carbomer, pullulan, carrageenan, sodium alginate, acrylate polymer or copolymer, water-soluble cellulose-based polymer, xanthan gum, polyvinyl alcohol and combination thereof.

13. The patch according to claim 11, wherein the drug layer further comprises a plasticizer selected from the group consisting of polypropylene glycol, glycerin, or polyethylene glycol, castor oil, PEG-60 hydrogenated castor oil, PEG-40 hydrogenated castor oil, and combinations thereof.

14. The patch according to claim 11, wherein the water-soluble, water-swellable or water-dispersed polymer comprised in the second drug layer is 40 to 70% by weight relative to the weight of the total drug layers.

15. The patch according to claim 1, wherein the backing layer comprises a water-insoluble polymer having a hydrophilic functional group of a hydroxyl group or carboxyl group, a thermoplastic, or a mixture thereof.

16. The patch according to claim 15, wherein the water-insoluble polymer is selected from the group consisting of ethyl cellulose, cellulose acetate, a copolymer of polymethylmethacrylate, a copolymer of acetate-polyvinyl pyrrolidone, and combination thereof.

17. The patch according to claim 15, wherein the thermoplastic is selected from the group consisting of polyethylene, polyethylene terephthalate, polyvinyl chloride, polyvinylidene chloride, polystyrene, polypropylene, and combinations thereof.

18. The patch according to claim 1, wherein the reticular structure is formed by polymer filaments selected from the group consisting of acryl filaments, polyester filaments, nylon filaments, polypropylene filaments, polybutylene terephthalate filaments, ethylene vinyl acetate filaments, and combination thereof.

19. The patch according to claim 18, wherein the reticular structure comprises an embo pattern formed by polyethylene filaments.

20. The patch according to claim 1, wherein the active ingredient is a teeth whitening compound.

* * * * *